(12) United States Patent
Choi

(10) Patent No.: US 10,794,884 B2
(45) Date of Patent: Oct. 6, 2020

(54) CALIBRATION DEVICE AND GAS COMPONENT ANALYZING APPARATUS INCLUDING THE SAME

(71) Applicant: iSenLab Inc., Seongnam-si, Gyeonggi-do (KR)

(72) Inventor: Yong-sahm Choi, Seongnam-si (KR)

(73) Assignee: iSenLab Inc., Seongnam-si, Gyeonggi-do (KR)

( * ) Notice: Subject to any disclaimer, the term of this patent is extended or adjusted under 35 U.S.C. 154(b) by 200 days.

(21) Appl. No.: 15/554,008

(22) PCT Filed: Mar. 27, 2017

(86) PCT No.: PCT/KR2017/003271
§ 371 (c)(1),
(2) Date: Aug. 28, 2017

(87) PCT Pub. No.: WO2017/171331
PCT Pub. Date: Oct. 5, 2017

(65) Prior Publication Data
US 2018/0172653 A1  Jun. 21, 2018

(30) Foreign Application Priority Data

Mar. 28, 2016 (KR) .................... 10-2016-0036947

(51) Int. Cl.
*G01N 33/00* (2006.01)
*G01N 21/76* (2006.01)
(Continued)

(52) U.S. Cl.
CPC .......... *G01N 33/0006* (2013.01); *G01N 1/20* (2013.01); *G01N 1/2035* (2013.01); *G01N 1/22* (2013.01);
(Continued)

(58) Field of Classification Search
CPC combination set(s) only.
See application file for complete search history.

(56) References Cited

U.S. PATENT DOCUMENTS 5,739,038 A * 4/1998 Burrows ................ G01N 21/31
  422/199
10,101,298 B1 * 10/2018 Zhang ..................... G01N 27/66
(Continued)

FOREIGN PATENT DOCUMENTS

| JP | 08-005619 A | 1/1996 |
|----|-------------|--------|
| JP | 2004-108981 A | 4/2004 |

(Continued)

OTHER PUBLICATIONS

International Search Report for PCT/KR2017/003271 dated Jun. 28, 2017 from Korean Intellectual Property Office.

*Primary Examiner* — Peter J Macchiarolo
*Assistant Examiner* — Mohammed E Keramet-Amircolai
(74) *Attorney, Agent, or Firm* — Novick, Kim & Lee, PLLC; Jae Youn Kim; Jihun Kim

(57) ABSTRACT

A calibration device for calibrating a gas component analyzing apparatus for analyzing by detecting a component of a sample gas by a detector, which is separated as a single component through a separation unit, wherein the separation unit is connected to a supply tube providing a gas thereto, and a plurality of calibration gases that are adjusted to have different concentrations from each other through adjustment of a volume ratio of a calibration gas having one concentration are sequentially provided to the separation unit through the supply tube.

7 Claims, 16 Drawing Sheets

(51) Int. Cl.
    *G01N 1/20*     (2006.01)
    *G01N 1/22*     (2006.01)

(52) U.S. Cl.
    CPC ....... *G01N 21/76* (2013.01); *G01N 2001/205* (2013.01)

(56) References Cited

U.S. PATENT DOCUMENTS

| | | | |
|---|---|---|---|
| 2004/0056044 A1 | 3/2004 | Hirahara et al. | |
| 2010/0220320 A1* | 9/2010 | Baba | G01N 21/67 356/213 |
| 2011/0119012 A1* | 5/2011 | Buess | G01N 29/30 702/86 |
| 2014/0331737 A1* | 11/2014 | Kaneblei | G01N 33/0006 73/1.06 |
| 2014/0349408 A1* | 11/2014 | Skourlis | G01N 33/0006 436/149 |
| 2015/0293066 A1* | 10/2015 | Hale | G01N 33/0006 73/1.02 |
| 2015/0323511 A1* | 11/2015 | Hendry | A61B 5/1495 73/1.06 |
| 2016/0349226 A1* | 12/2016 | Chauhan | G01N 33/0006 |
| 2017/0089876 A1* | 3/2017 | Otaki | G01N 33/0006 |
| 2017/0168033 A1* | 6/2017 | Yoshimura | F01N 3/033 |
| 2018/0003684 A1* | 1/2018 | Kerr | G01N 33/0006 |
| 2018/0074029 A1* | 3/2018 | DeVries | G01N 33/0006 |
| 2018/0074030 A1* | 3/2018 | DeVries | G01N 33/0006 |
| 2018/0267003 A1* | 9/2018 | Johnson | G01N 33/0006 |
| 2018/0335410 A1* | 11/2018 | Martens | G01N 33/0006 |
| 2019/0094195 A1* | 3/2019 | Gentner | G01N 33/0047 |
| 2019/0113491 A1* | 4/2019 | Xie | G01N 27/66 |

FOREIGN PATENT DOCUMENTS

| | | |
|---|---|---|
| JP | 2006-003115 A | 1/2006 |
| KR | 10-2008-0029061 A | 4/2008 |
| KR | 10-0983827 B1 | 9/2010 |
| KR | 10-1359940 B1 | 2/2014 |

\* cited by examiner

-- Prior Art --

[FIG. 2]
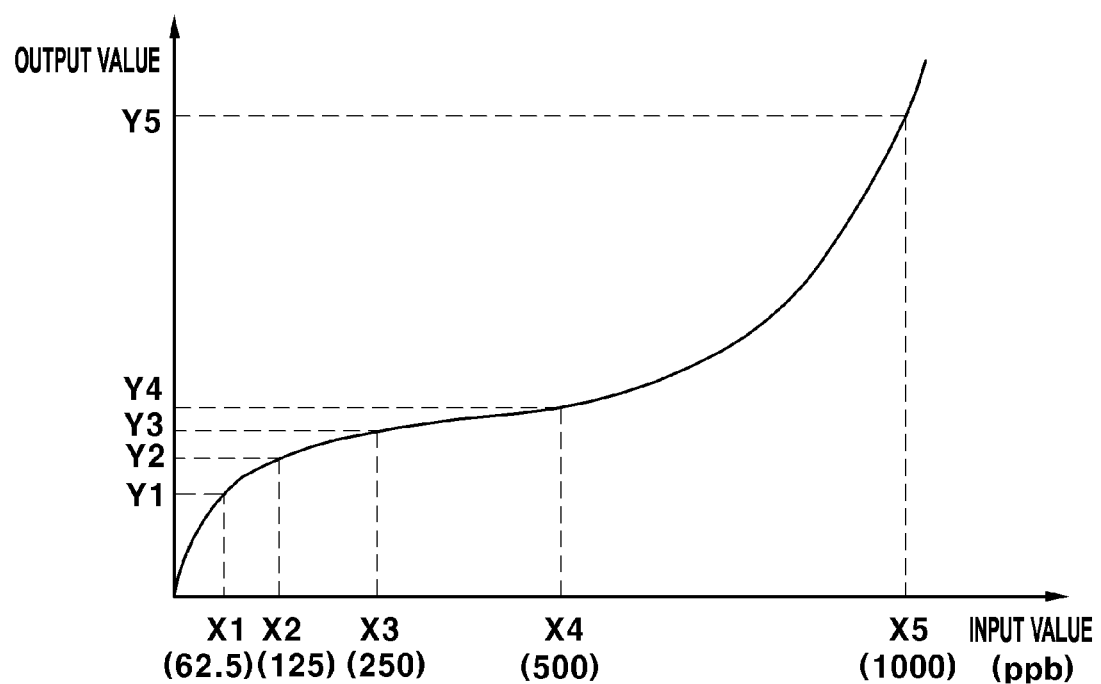

[FIG. 3]
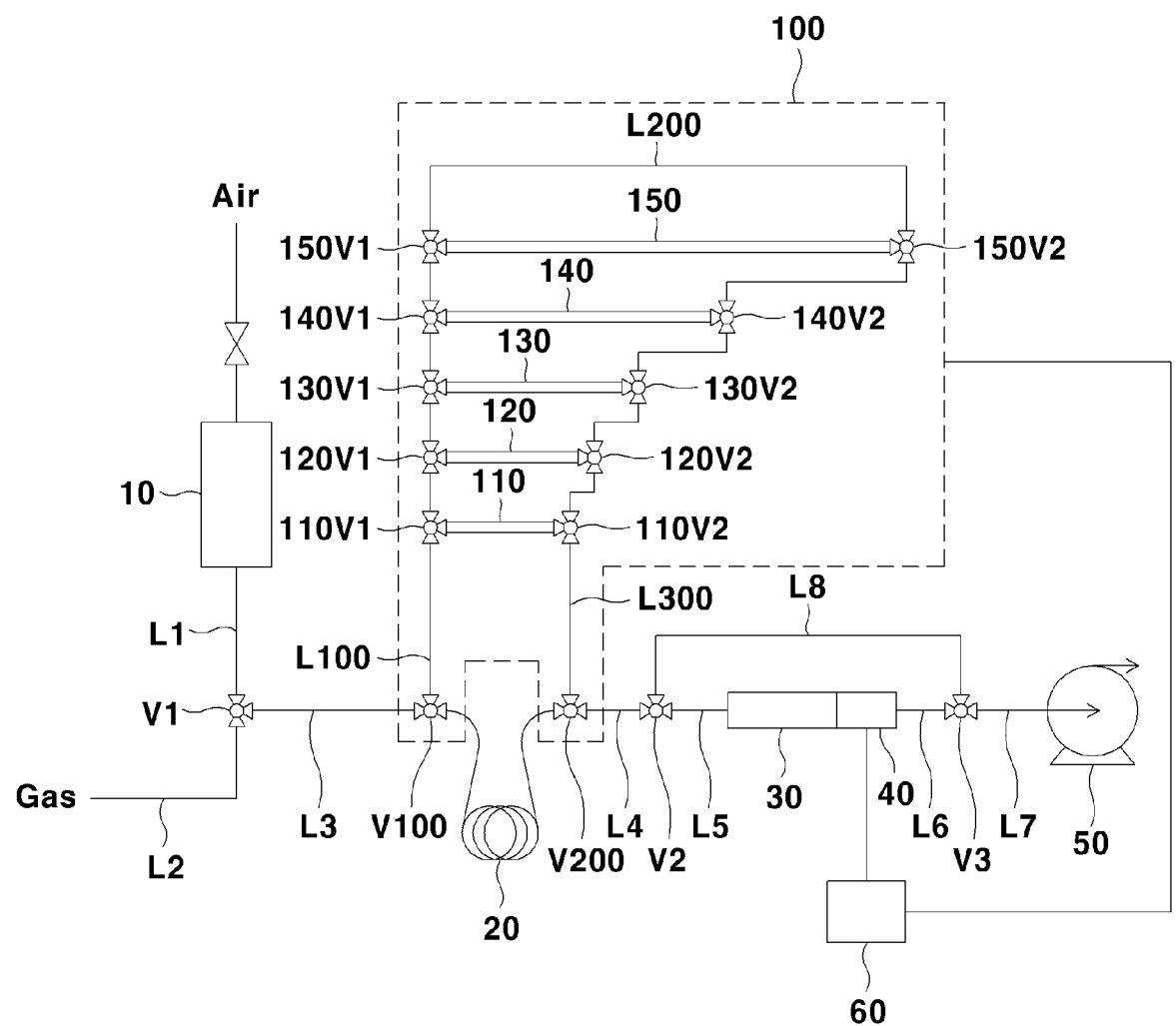

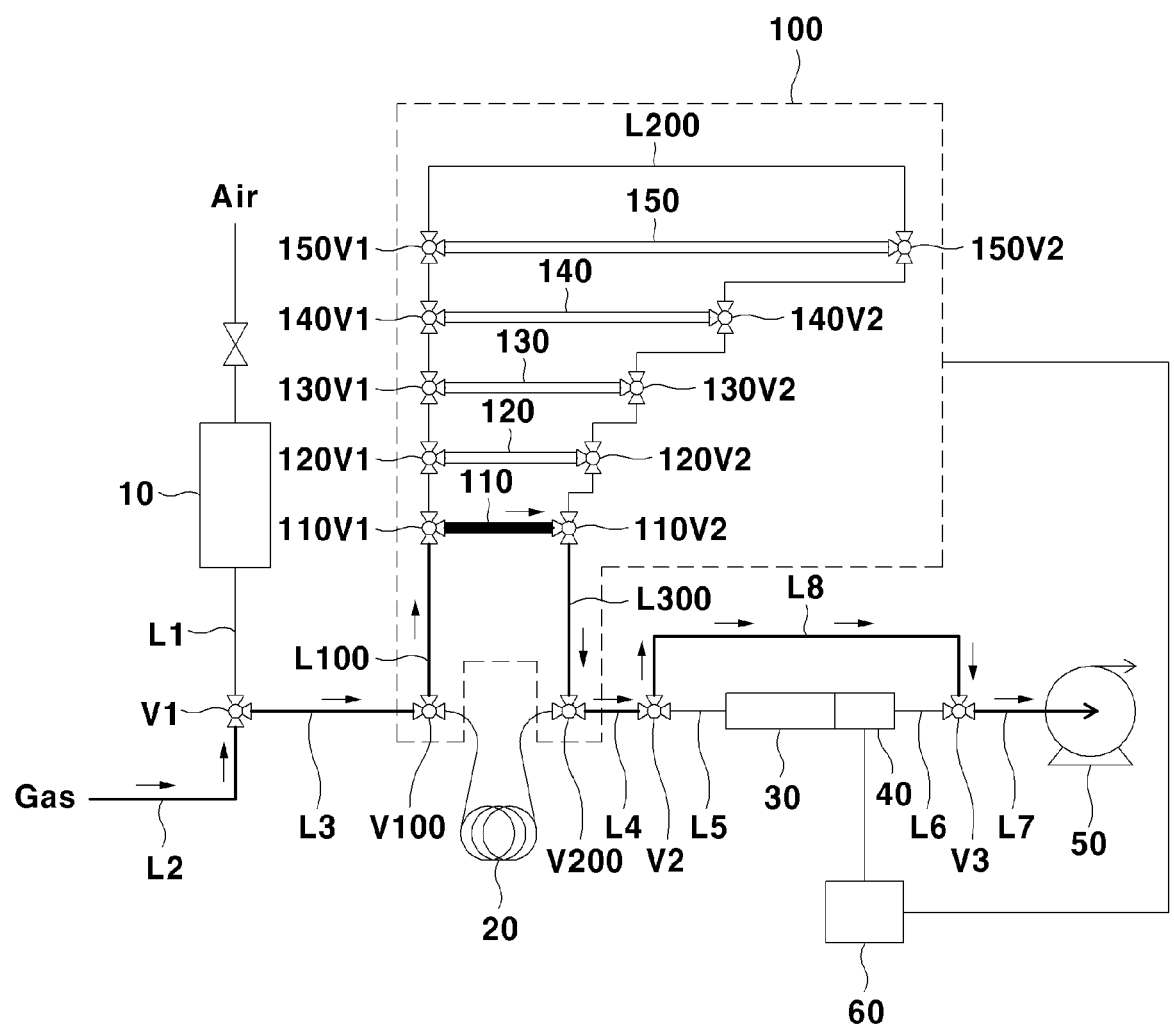
[FIG. 4]

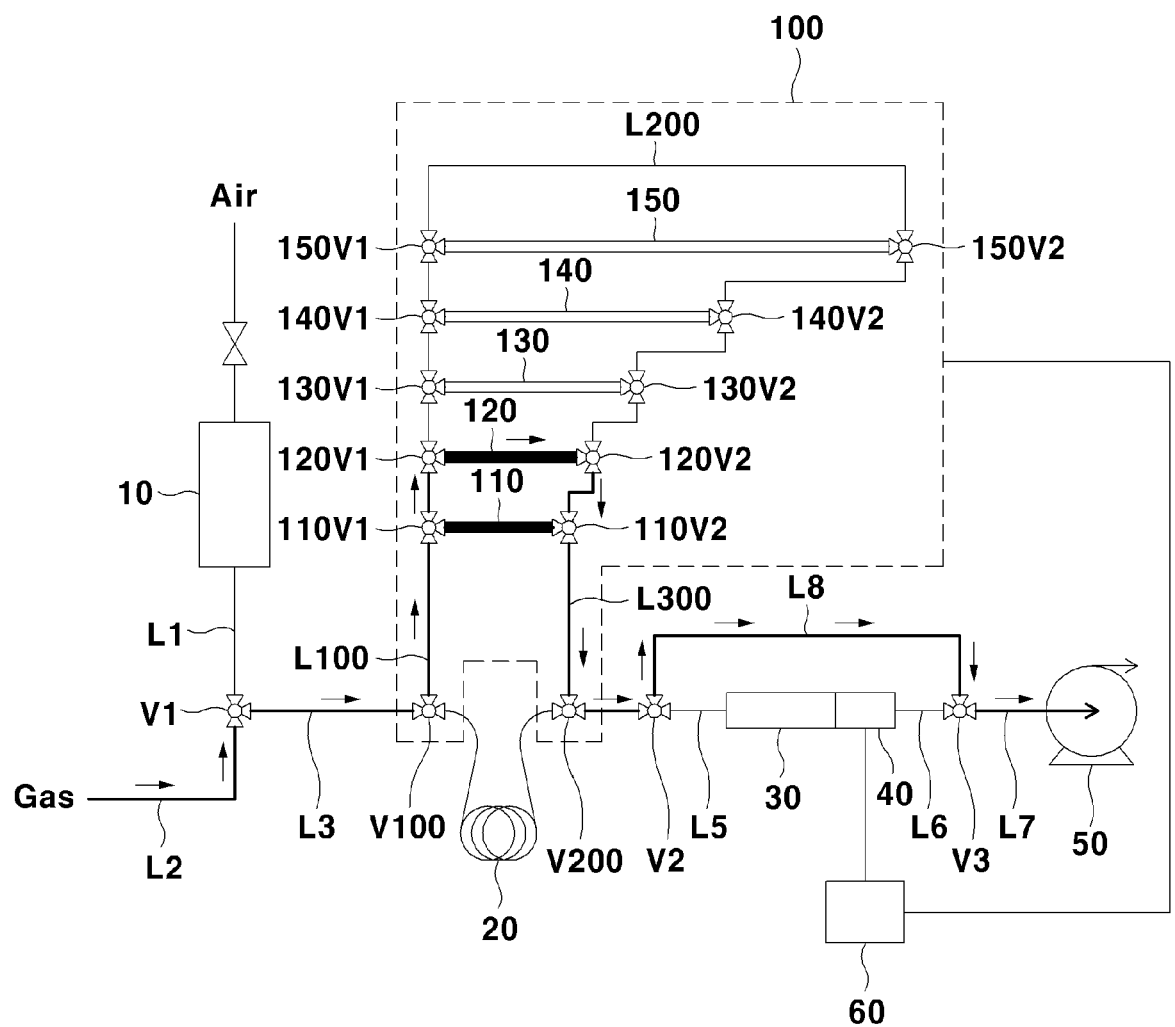
[FIG. 5]

[FIG. 6]
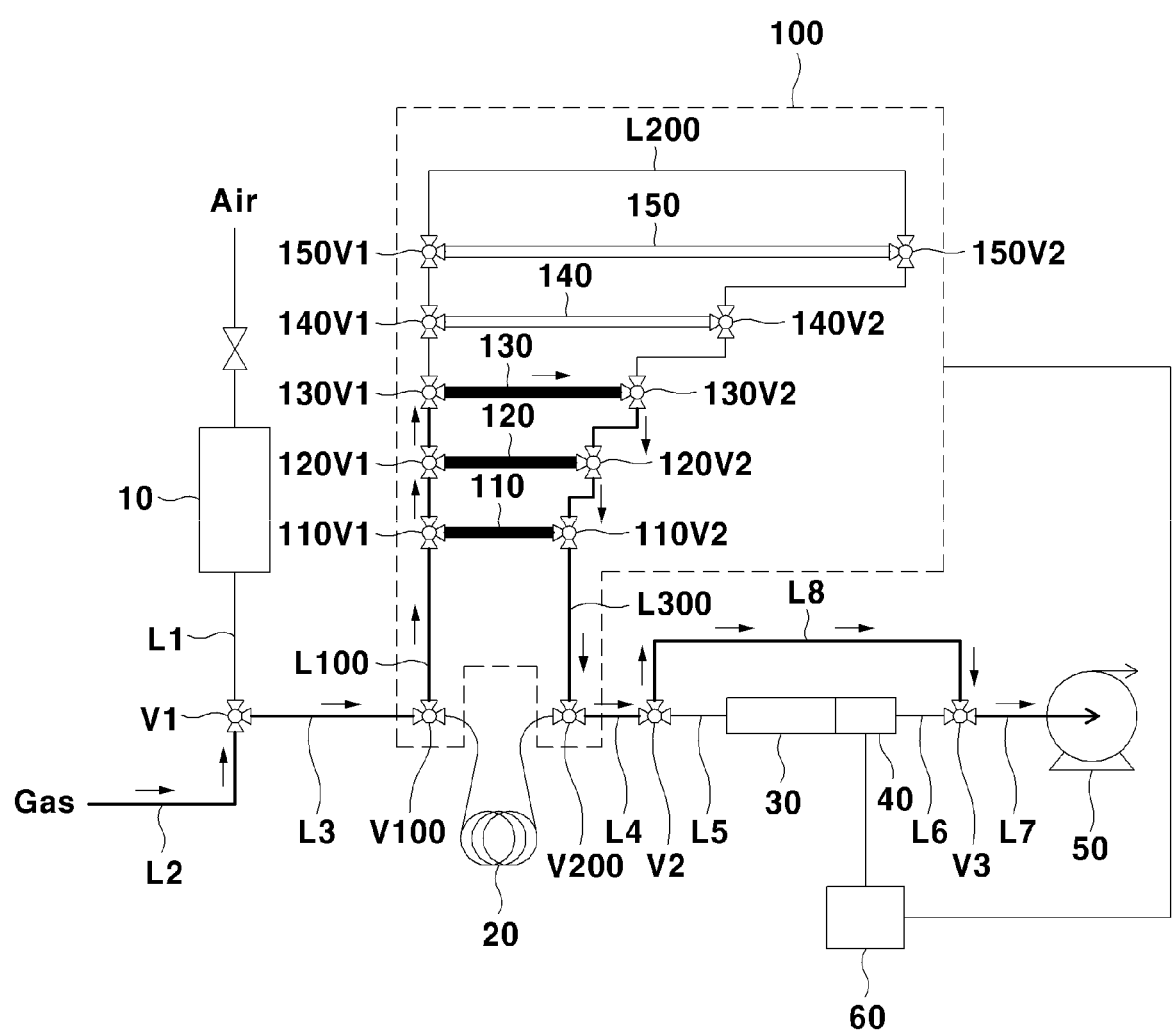

[FIG. 7]
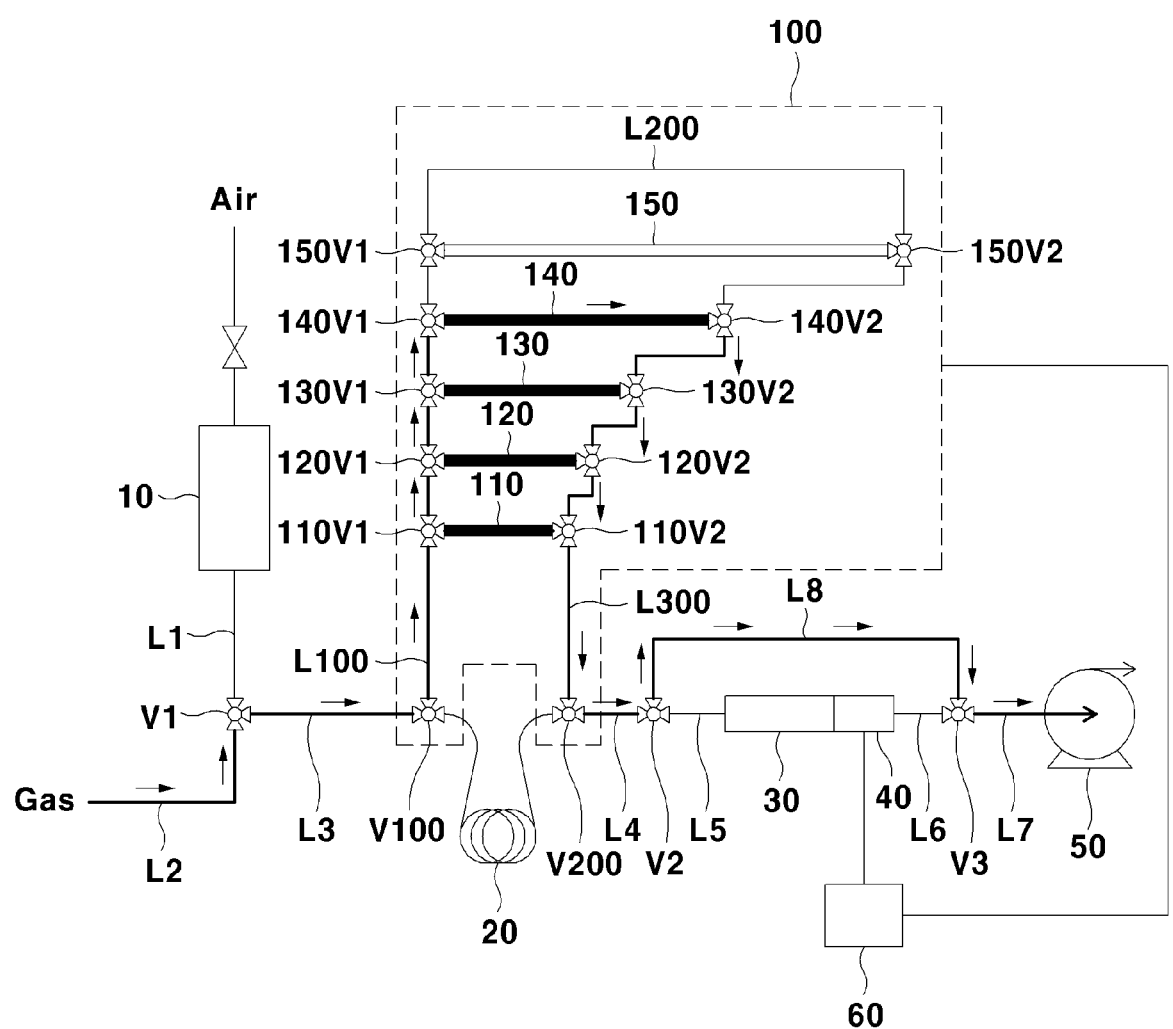

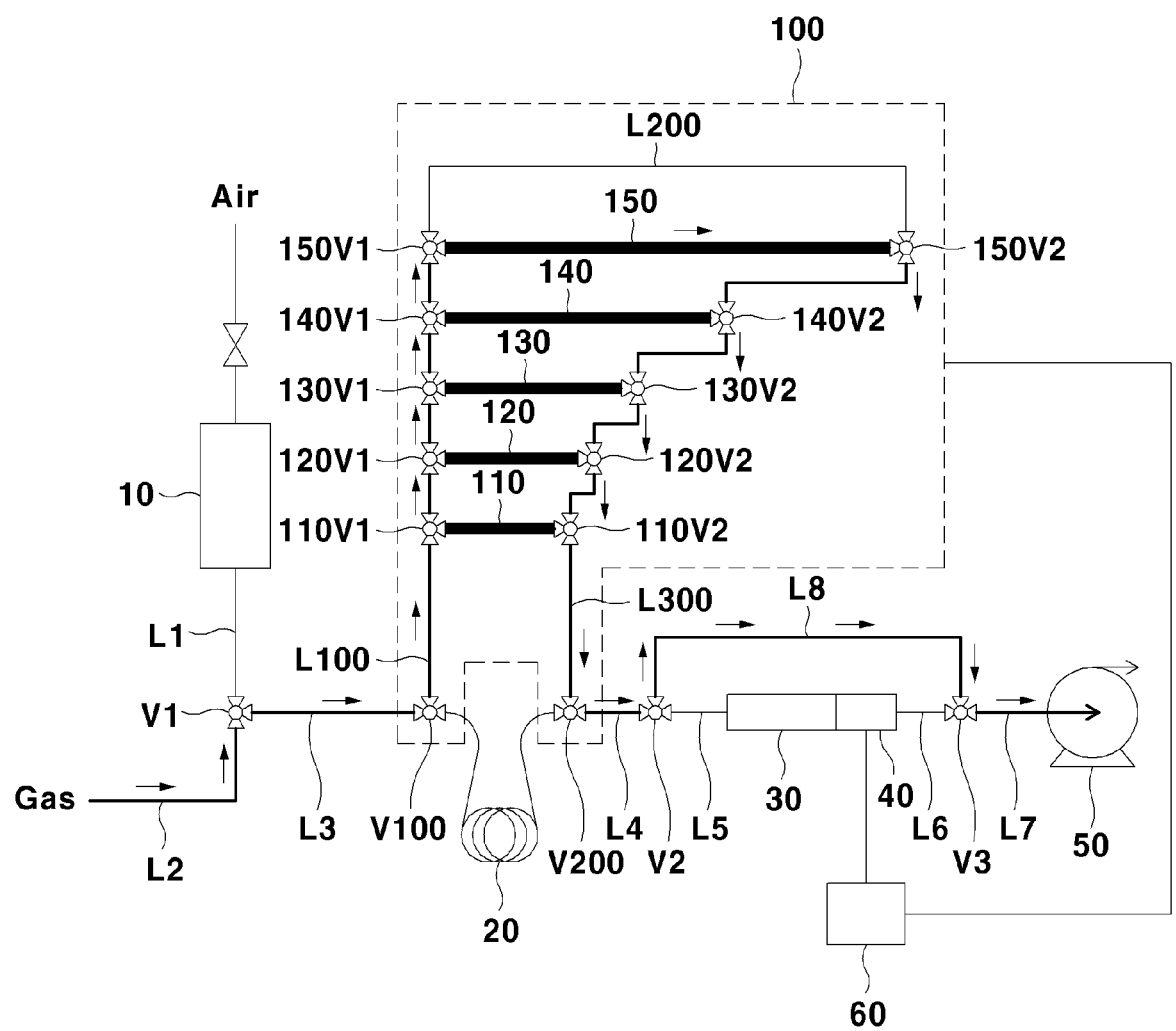
[FIG. 8]

[FIG. 9]
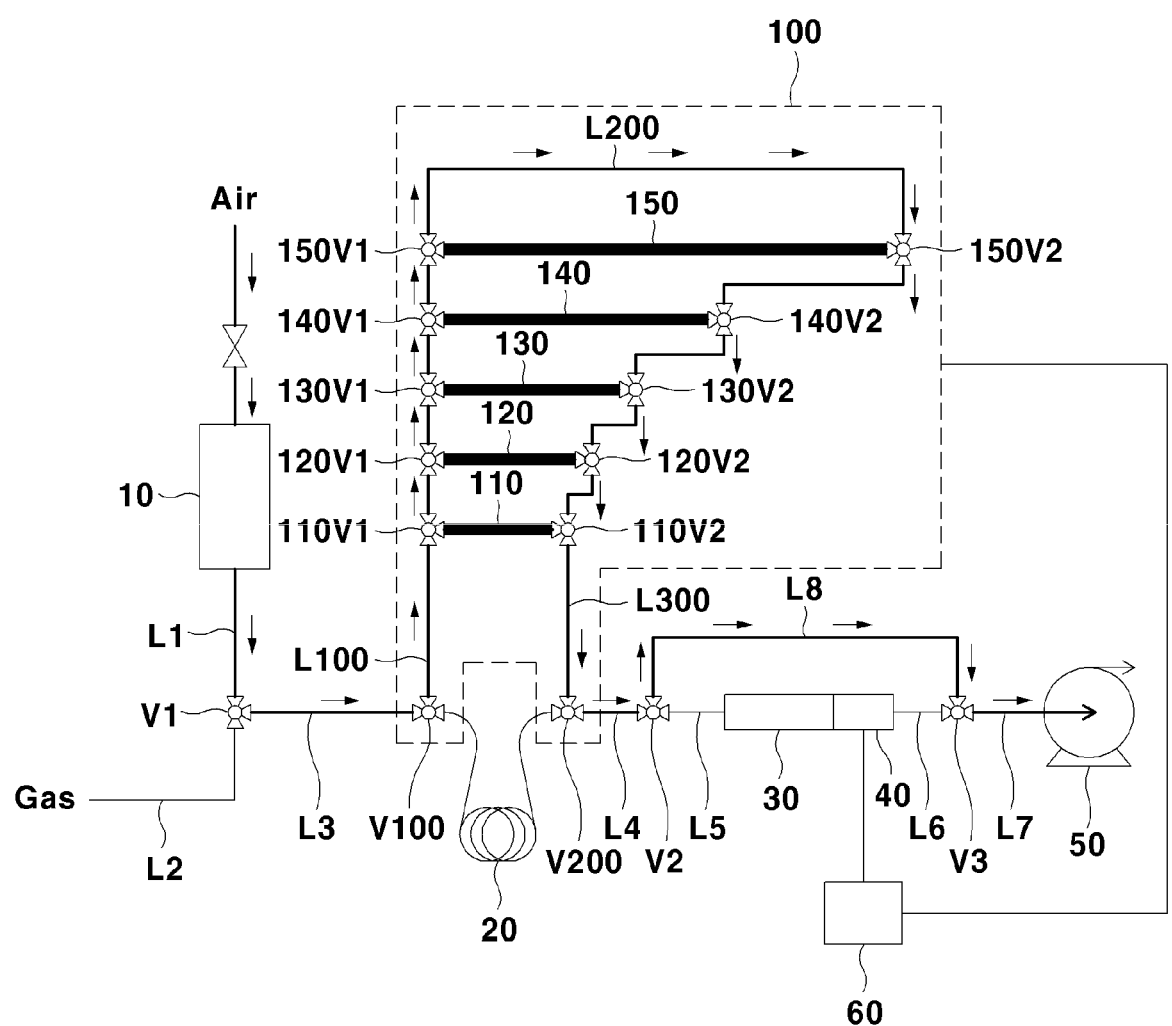

[FIG. 10]
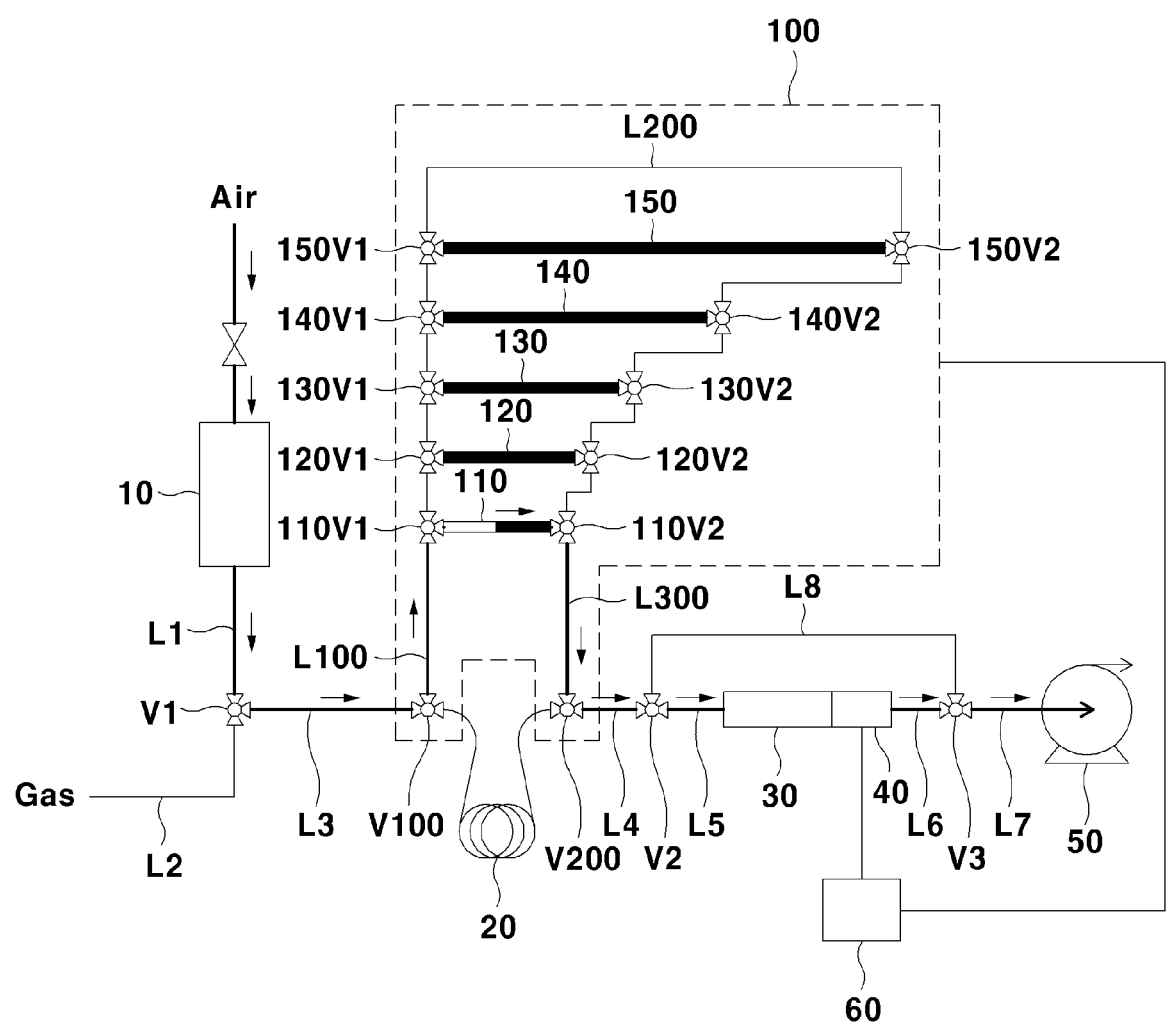

[FIG. 11]
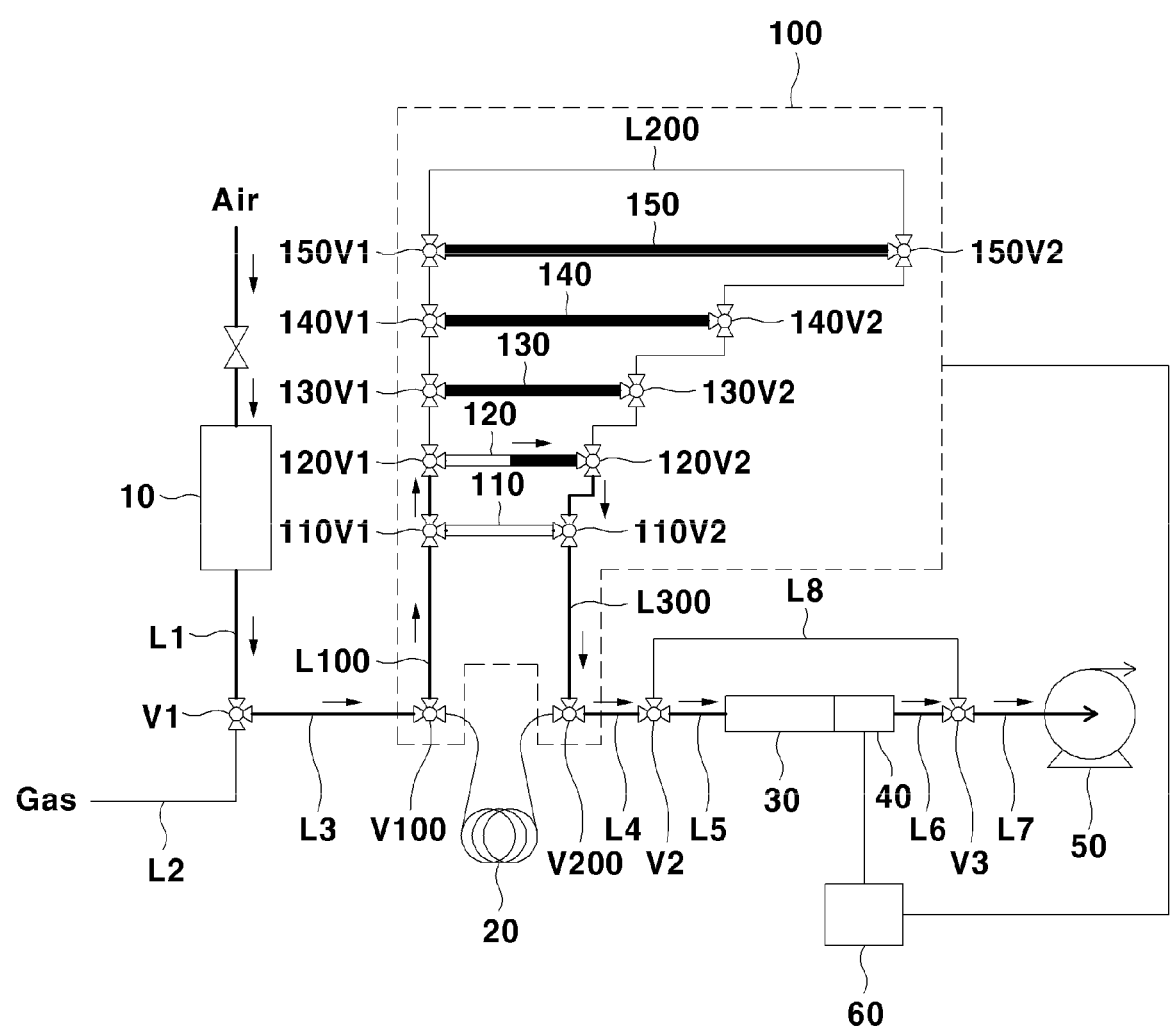

[FIG. 12]
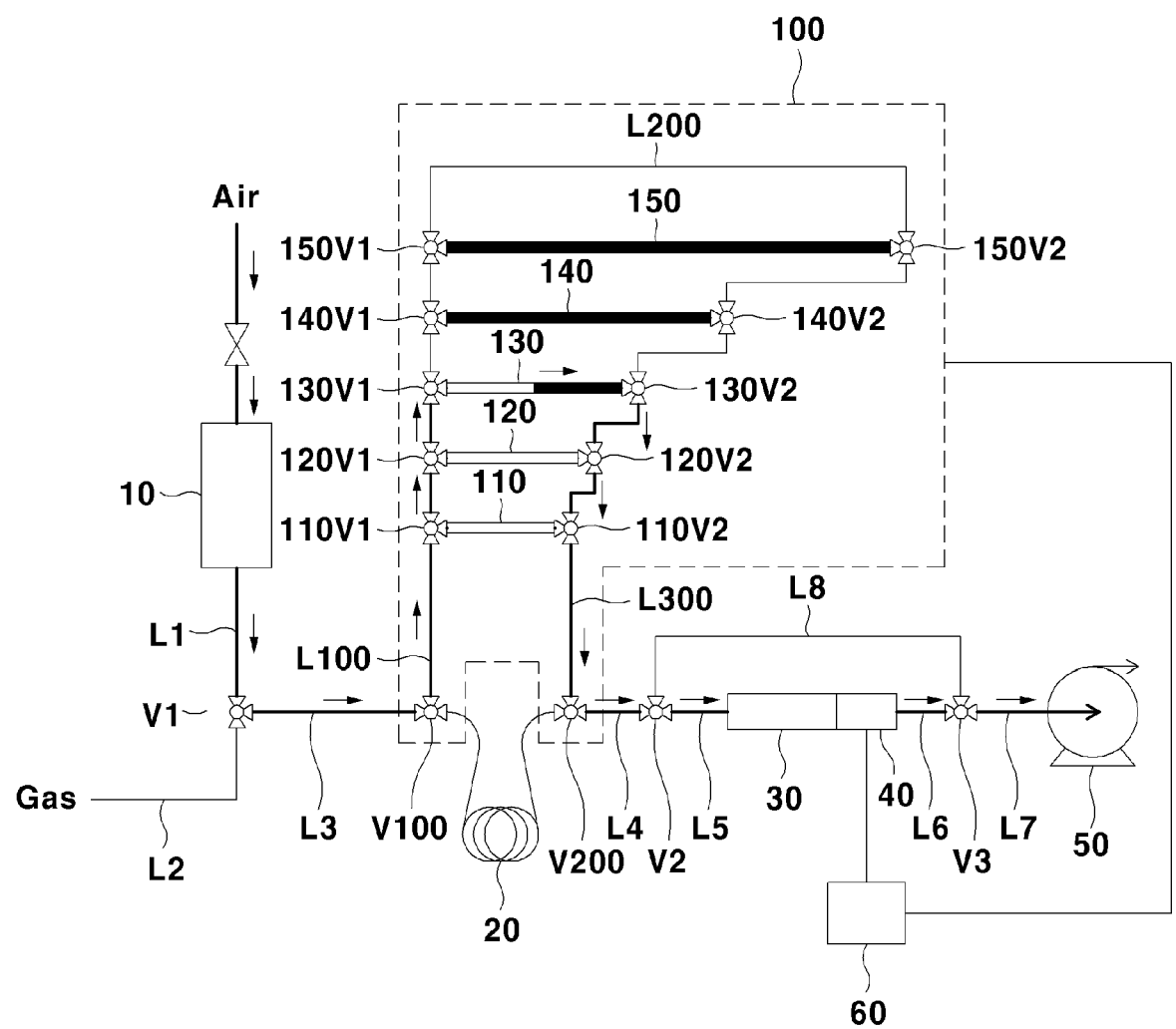

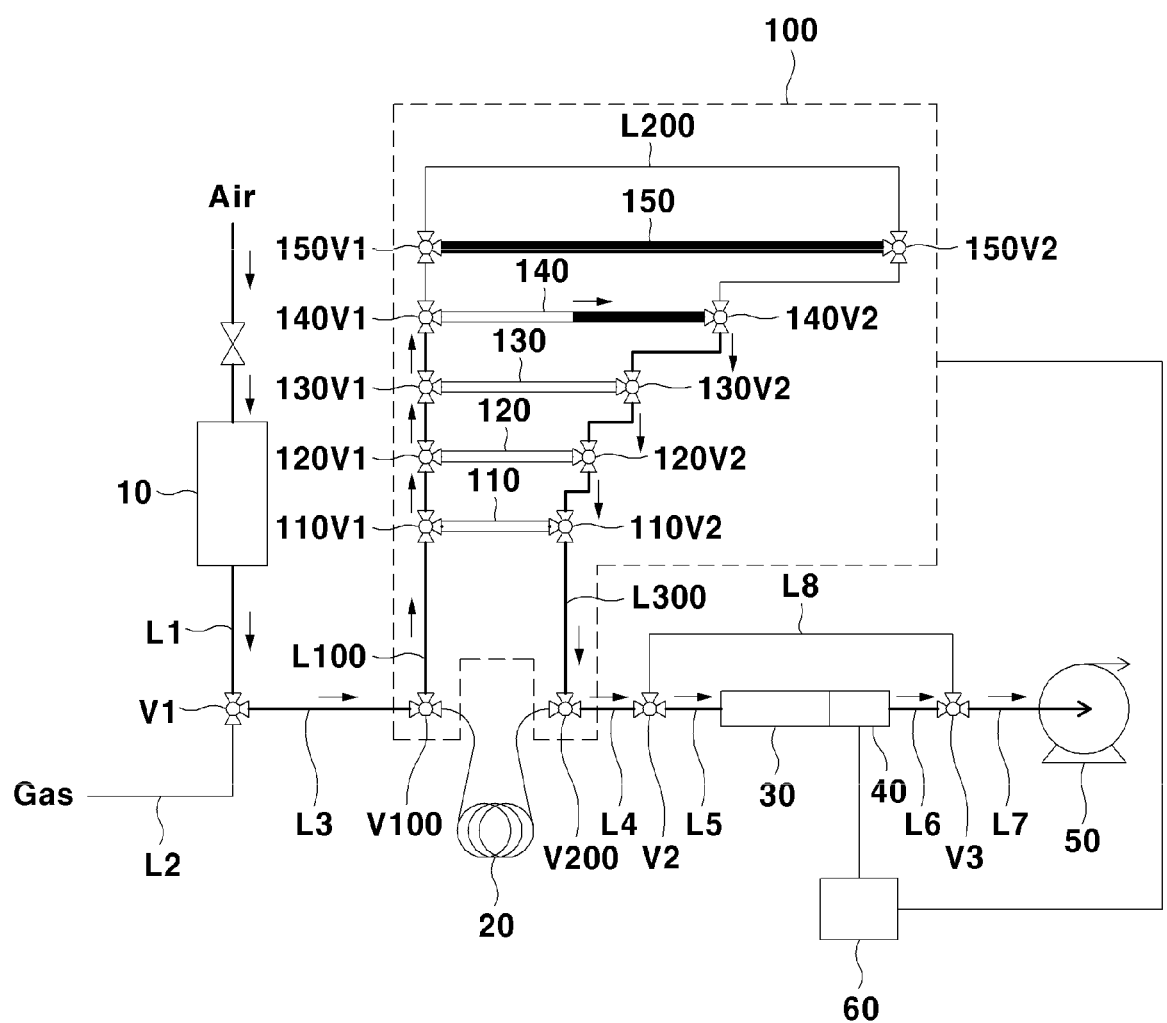
[FIG. 13]

[FIG. 14]
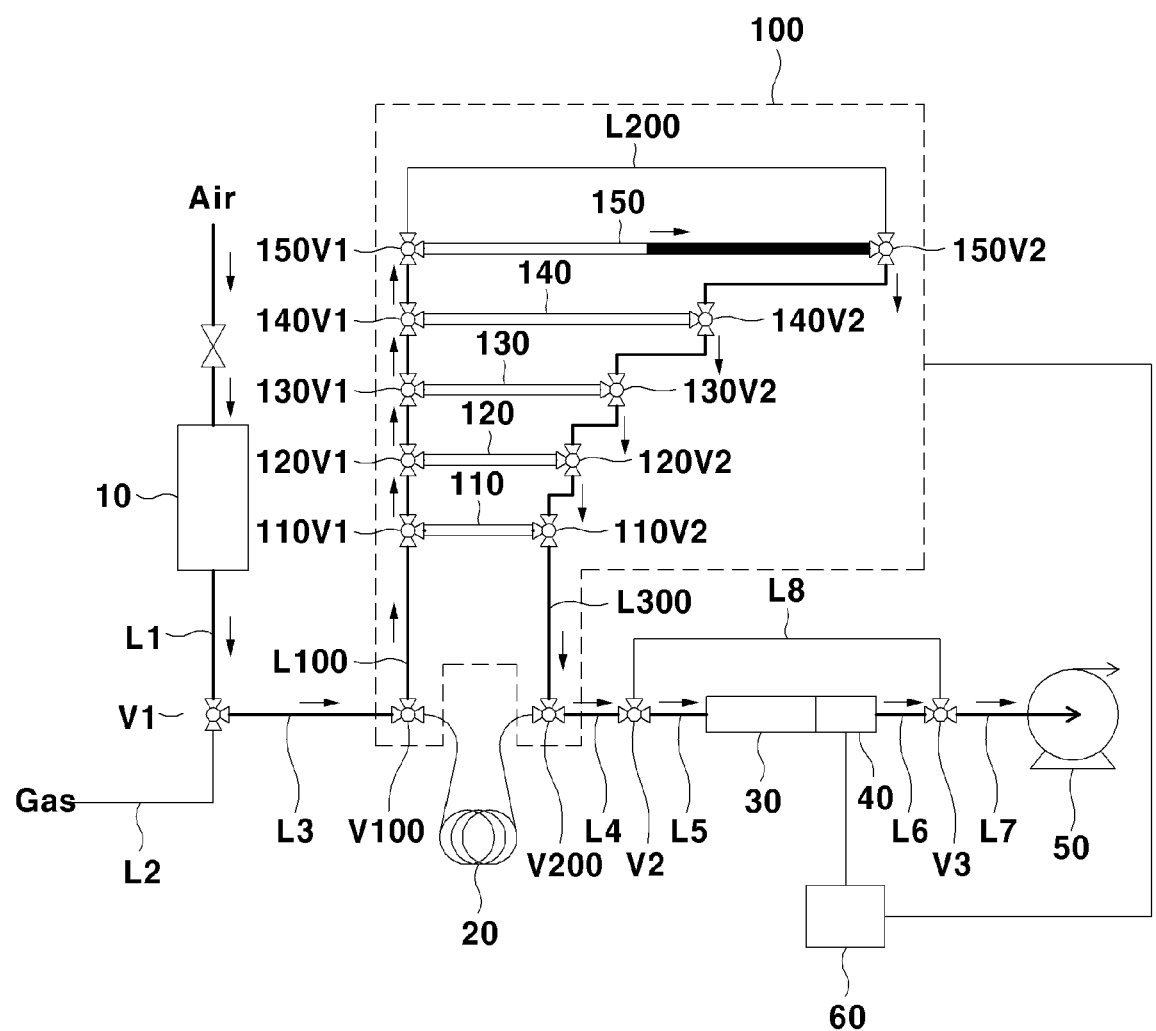

[FIG. 15]
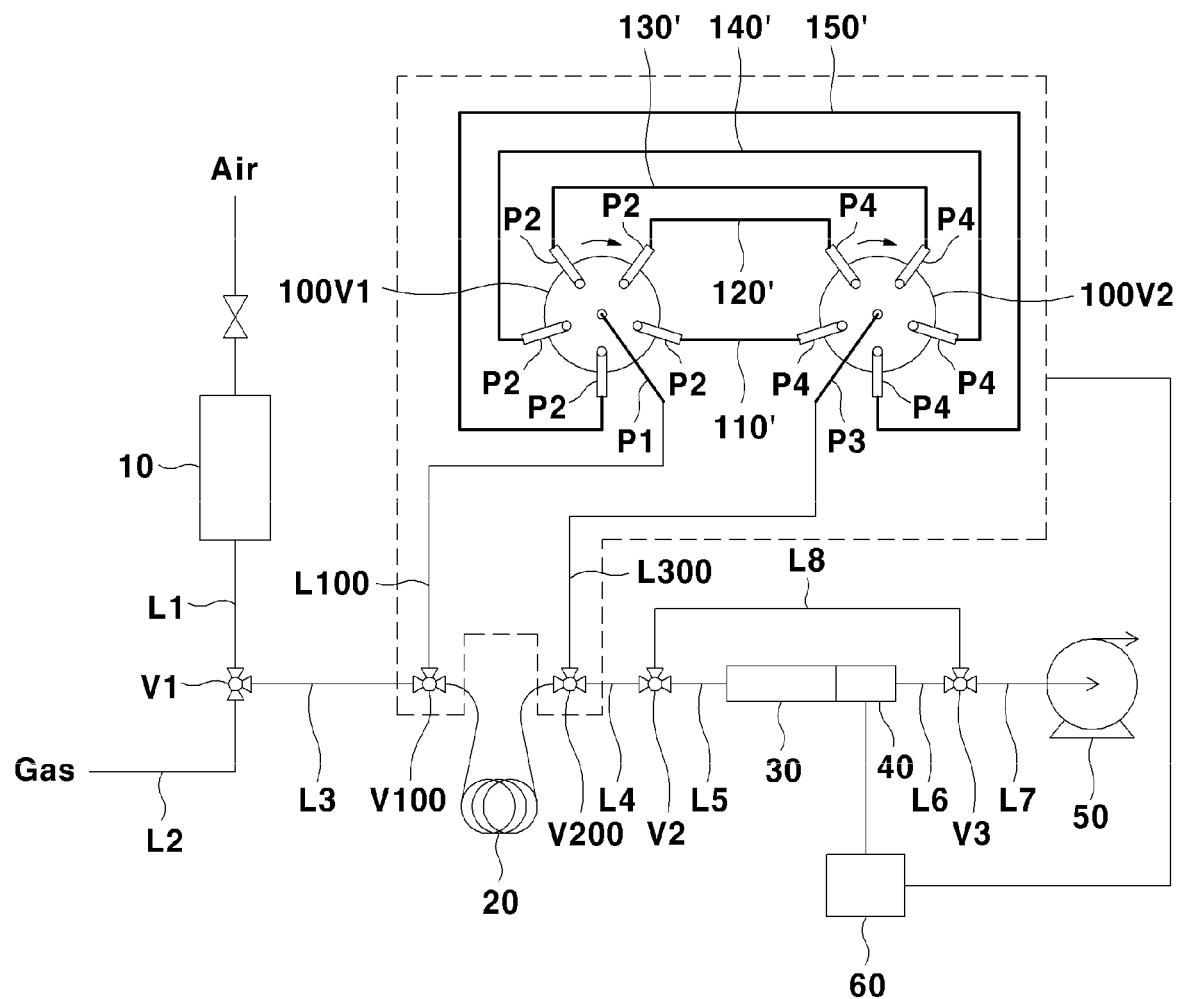

[FIG. 16]
(a)
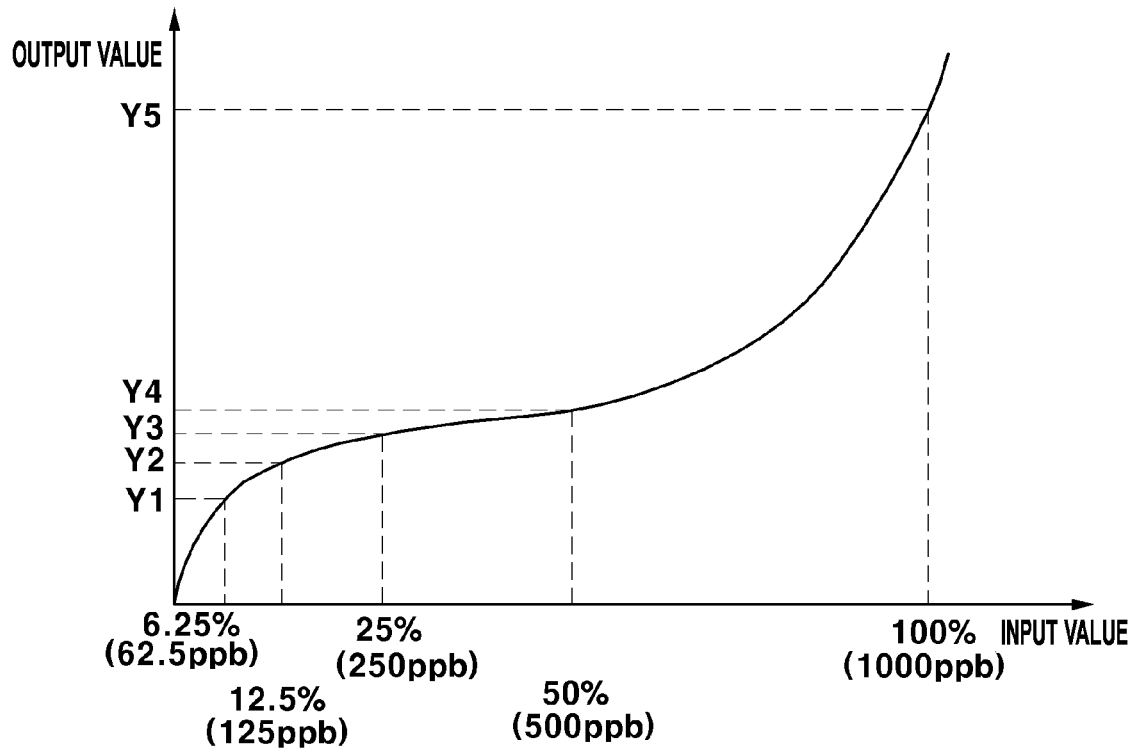
(b)
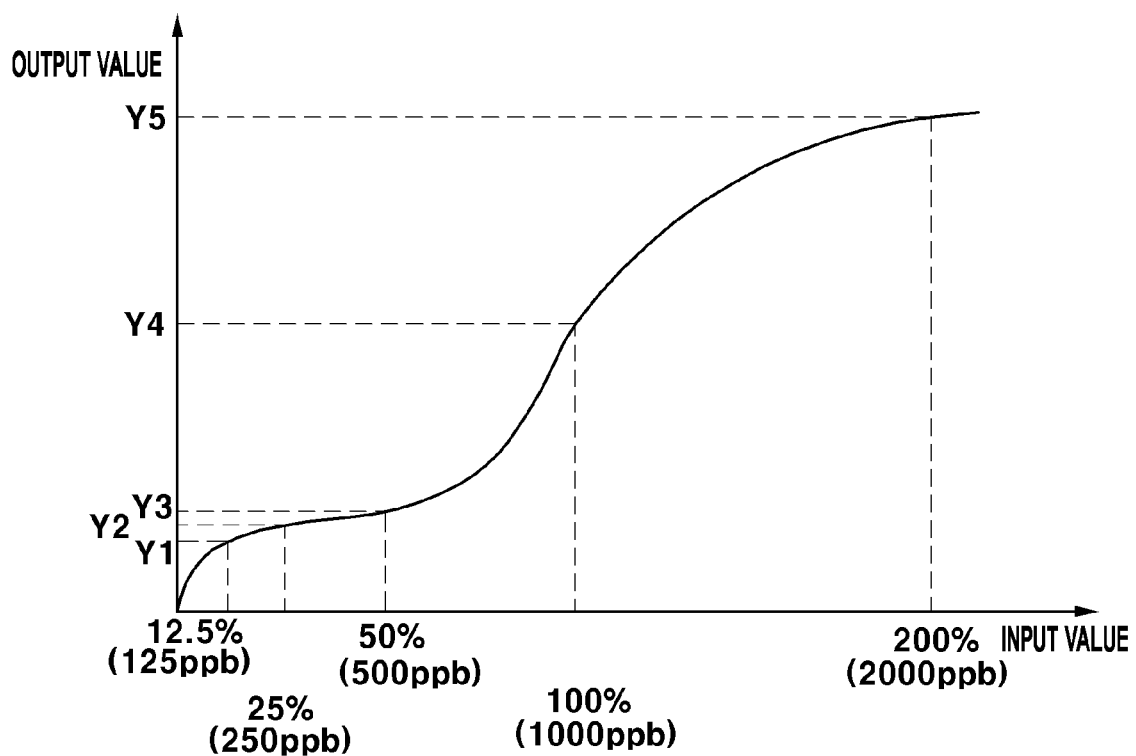

CALIBRATION DEVICE AND GAS COMPONENT ANALYZING APPARATUS INCLUDING THE SAME

CROSS REFERENCE TO PRIOR APPLICATIONS

This application is a National Stage Application of PCT International Patent Application No. PCT/KR2017/003271 filed on Mar. 27, 2017, under 35 U.S.C. § 371, which claims priority to Korean Patent Application No. 10-2016-0036947 filed on Mar. 28, 2016 which are all hereby incorporated by reference in their entirety.

TECHNICAL FIELD

The present invention relates to a calibration device and a gas component analyzing apparatus including the same, and more particularly, to a calibration device capable of simply and quickly performing a calibration work for improving accuracy and reliability on a measurement value of a gas component analyzing apparatus and a gas component analyzing apparatus including the same.

BACKGROUND ART

Calibration represents a quantification process of matching an absolute value of an output signal with respect to an input of a gas component analyzing apparatus with a standard signal.

The gas component analyzing apparatus measuring a concentration or a component of a gas by using a gas sensor is configured to measure the concentration or the component of the gas through the gas sensor.

The gas sensor is an element for measuring the concentration or the component of a gas by using a chemical method such as chemiresistive sensor. A calibration work is necessary for the gas sensor provided in the gas component analyzing apparatus before analyzing a component by using the gas component analyzing apparatus due to a sensitivity deviation generated during sensor manufacturing. Through this calibration work, a measurement value of the gas sensor may be corrected to enhance accuracy and reliability on the measurement value.

In general, the calibration work is performed such that a plurality of standard gases having different concentrations are prepared, and the standard gases are sequentially injected into the gas component analyzing apparatus to measure a signal and compare the measured signal with a standard value as illustrated in FIG. 1.

For example, the above-described process is repeatedly performed for each of concentrations of the standard gases, through this, the measured signals are stored, output signals with respect to input signals are calculated by a worker to produce a calibration equation, and the gas component analyzing apparatus is calibrated on the basis of the produced calibration equation.

In detail, the calibration gas having a concentration of X1 may be injected into the gas component analyzing apparatus to acquire the output signal of Y1 outputted from the gas sensor, the calibration gas having a concentration of X2 may be injected into the gas component analyzing apparatus to acquire the output signal of Y2 outputted from the gas sensor, the calibration gas having a concentration of X3 may be injected into the gas component analyzing apparatus to acquire the output signal of Y3 outputted from the gas sensor, the calibration gas having a concentration of X4 may be injected into the gas component analyzing apparatus to acquire the output signal of Y4 outputted from the gas sensor, and the calibration gas having a concentration of X5 may be injected into the gas component analyzing apparatus to acquire the output signal of Y5 outputted from the gas sensor.

Through the above-described process, the calibration data in which X and Y are matched such that 'X1->Y1', 'X2->Y2', 'X3->Y3', 'X4->Y4', 'X5->Y5' may be acquired, and, through the calibration data, the calibration equation such as a mathematical equation below may be produced.

$$Y = aX^3 + bX^2 + cX + d \qquad \text{<Mathematical equation 1>}$$

However, since the process of acquiring the measurement signal by repeatedly injecting the plurality of standard gases having different concentrations into the gas component analyzing apparatus is performed manually by the worker, the calibration work is inconvenient and takes a long time, and the exact calibration is hardly performed.

PRIOR ART DOCUMENTS

Korean Registered Patent No. 10-0983827 (Registration date: Sep. 16, 2010)

DISCLOSURE OF THE INVENTION

Technical Problem

The present invention provides a calibration device capable of simply and quickly performing a calibration work for improving accuracy and reliability on a measurement value of a gas component analyzing apparatus and a gas component analyzing apparatus including the same.

Technical Solution

According to an embodiment of the present invention, a calibration device calibrates a gas component analyzing apparatus for analyzing by detecting a component of a sample gas by a detector, which is separated as a single component through a separation unit like a gas chromatographic column. Here, the separation unit is connected to a supply tube providing a gas thereto, and a plurality of calibration gases that are adjusted to have different concentrations from each other through adjustment of a volume ratio of a calibration gas having one concentration are sequentially provided to the separation unit through the supply tube.

Desirably, the calibration device may include: one side connection part selectively connected to one point of the supply tube; the other side connection part selectively connected to the other point of the supply tube; and a calibration line part including a plurality of connection tubes parallel-connecting the one side connection part to the other side connection part in different paths from each other. Here, the plurality of connection tubes have different volumes from each other.

Desirably, the one side connection part may include one side valve provided on the supply tube and an input tube selectively communicating with the supply tube through the one side valve, and the other side connection part may include the other side valve provided on the supply tube and an output tube selectively communicating with the supply tube through the other side valve.

Desirably, the calibration line part may include a plurality of input side calibration valves that are serially arranged on the input tube and a plurality of output side calibration valves that are serially arranged on the output tube, and the plurality of connection tubes may one-to-one connect the plurality of input side calibration valves to the plurality of output side calibration valves each other.

Desirably, the calibration device may further include a control unit controlling the one side valve, the other side valve, the input side calibration valve, and the output side calibration valve. Here, the one side valve, the other side valve, the input side calibration valve, and the output side calibration valve may be solenoid valves.

Desirably, the control unit may sequentially fill a calibration gas to the plurality of connection tubes through controlling the input side calibration valve and the output side calibration valve in a state in which a gas is introduced into the calibration line part through controlling the one side valve and the other side valve.

Desirably, the calibration device may further include an exhaust tube connecting an end of the one side connection part to an end of the other side connection part. Here, the control unit may circulate an air through the input tube, the exhaust tube, and the output tube to discharge and remove a gas except for a gas in the plurality of connection tubes in a state in which a gas for calibrating the plurality of connection tubes is completely filled.

Desirably, the control unit may perform detection by sequentially transferring the gas in the plurality of connection tubes to a detector so as to acquire calibration data.

Desirably, the calibration line part may include: one input port communicating with the input tube and an input side multi-directional selection valve having a plurality of output ports that are selectively connected to the input port; and one output port communicating with the output tube and an output side multi-directional selection valve having and a plurality of input ports that are selectively connected to the output port. Here, the plurality of connection tubes may one-to-one connect the plurality of output ports of the input side multi-directional selection valve to the plurality of input ports of the output side multi-directional selection valve each other.

Desirably, a connection tube having a largest volume among the plurality of connection tubes may have the same volume as that of a sampling loop provided in the gas component analyzing apparatus.

Desirably, a connection tube having a largest volume among the plurality of connection tubes may have a volume greater than that of a sampling loop provided in a gas component analyzing apparatus.

According to another embodiment of the present invention, a gas component analyzing apparatus includes the above-described calibration device integrally embedded or detachably provided therein.

Advantageous Effects

As described above, the present invention has an advantage in that the calibration work for improving the accuracy and the reliability on the measurement value of the gas component analyzing apparatus may be simply and quickly performed.

Also, as the gas in the portion except for the plurality of connection tubes in which the calibration gas is filled before the calibration process through controlling the control unit is discharged and removed, the degree of precision of the calibration may increase.

Also, as the volume ratio between the connection tube having the largest volume and the sampling loop is appropriately adjusted, the concentration range that may be calibrated by using the calibration gas may be selectively adjusted. For example, while the range greater than the concentration range of the used calibration gas is impossible to be calibrated in the related art, the concentration greater than the used concentration may be calibrated according to the present invention.

BRIEF DESCRIPTION OF THE DRAWINGS

FIG. 2 is a graph showing a calibration equation for calibrating a gas component analyzing apparatus.

FIG. 3 is a configuration view illustrating a configuration of a gas component analyzing apparatus including a calibration device according to an embodiment of the present invention.

FIGS. 4 to 9 are views illustrating a process of filling a calibration gas into the calibration device according to an embodiment of the present invention.

FIGS. 10 to 14 are views illustrating a process of measuring a signal for calibration through the calibration device according to an embodiment of the present invention.

FIG. 15 is a configuration view illustrating a configuration of a gas component analyzing apparatus including a calibration device according to another embodiment of the present invention.

FIG. 16 is a graph showing a calibration equation obtained by using the gas component analyzing apparatus including the calibration device according to an embodiment of the present invention.

MODE FOR CARRYING OUT THE INVENTION

Figure 1:
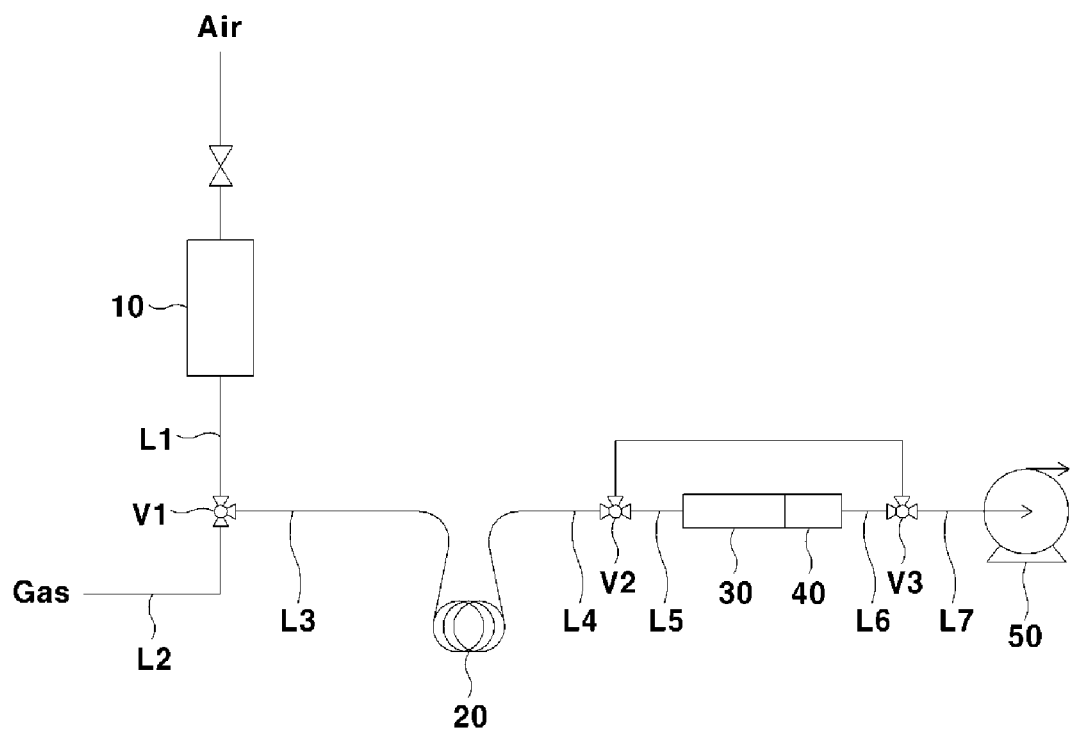
FIG. 1 is a configuration view of a conventional gas component analyzing apparatus.

The present invention may be embodied in different forms without being out of the scope, technical idea and essential features of the present invention. The preferred embodiments should be considered in descriptive sense only and are not for purposes of limitation.

It will be understood that although the terms of first and second are used herein to describe various elements, these elements should not be limited by these terms.

The terms are only used to distinguish one component from other components. For example, a first element referred to as a first element in one embodiment can be referred to as a second element in another embodiment.

The word 'and/or' means that one or more or a combination of relevant constituent elements is possible.

It will also be understood that when an element is referred to as being '"connected to" or "engaged with" another element, it can be directly connected to the other element, or intervening elements may also be present.

It will also be understood that when an element is referred to as being 'directly connected to' another element, there is no intervening elements.

In the following description, the technical terms are used only for explaining a specific exemplary embodiment while not limiting the present invention. The terms of a singular form may include plural forms unless referred to the contrary.

The meaning of 'include' or 'comprise' specifies a property, a number, a step, a process, an element, a component, or a combination thereof in the specification but does not exclude other properties, numbers, steps, processes, elements, components, or combinations thereof.

Unless terms used in the present disclosure are defined differently, the terms may be construed as meaning known to those skilled in the art.

Terms such as terms that are generally used and have been in dictionaries should be construed as having meanings matched with contextual meanings in the art. In this description, unless defined clearly, terms are not ideally, excessively construed as formal meanings.

Hereinafter, embodiments disclosed in this specification is described with reference to the accompanying drawings, and the same or corresponding components are given with the same drawing number regardless of reference number, and their duplicated description will be omitted.

Moreover, detailed descriptions related to well-known functions or configurations will be ruled out in order not to unnecessarily obscure subject matters of the present invention.

As illustrated in FIG. 1, a gas component analyzing apparatus includes a filter 10, a sampling loop 20, a separation unit 30 like a gas chromatographic column, a gas sensor 40, a pump 50, a first solenoid valve V1, a second solenoid valve V2, a third solenoid valve V3, a first tube line L1, a second tube line L2, a third tube line L3, a fourth tube line L4, a fifth tube line L5, a sixth tube line L6, and a seventh tube line L7.

The filter 10 is filled with a material adsorbing a polar molecule such as silica gel and activated carbon and a non-polar molecule to filter an air that is a carrier for an external gas.

The sampling loop 20 is made of a material to which a gas is difficult to be adsorbed, e.g., Teflon, and has a structure having a length that is long enough with respect to a diameter.

The sampling loop 20 sequentially pushes out a gas existing in advanced therein while collecting a gas and sequentially provides the collected gas to the separation unit 30 and the gas sensor 40 while measuring the gas.

The sampling loop 20 allows a gas collected for measurement to be collected at an exact volume. The gas is moved to the sampling loop 20 having a predetermined volume for a collecting time that is calculated in consideration of a suction speed of the pump 50, and gases excessive to a planned volume is block by operation of the solenoid valve that is closed according to a determined time, so that only the gas at the exact volume is remained in the sampling loop 20.

The separation unit 30 may be referred to as a gas chromatographic column. The separation unit 30 serves to separate various components in a mixed gas into each single component for chromatography analysis, respectively.

The gas sensor 40 is a sensor sequentially measuring the components of the gas that is separated by passing through the separation unit 30.

The pump 50 serves to allow the gas or the air to circulate and flow through the tube line.

Meanwhile, for the flow of the gas or the air, the first tube line L1, the second tube line L2, the third tube line L3, the fourth tube line L4, the fifth tube line L5, the sixth tube line L6, and the seventh tube line L7 are provided.

Also, to control a flow direction of the gas or the air, the first solenoid valve V1, the second solenoid valve V2, and the third solenoid valve V3 are provided.

Since the detailed configuration and operation of the above-described gas component analyzing apparatus are the same as or similar to those of the conventional gas component analyzing apparatus, detailed description will be omitted. Hereinafter, a calibration device 100 will be described in detail.

The calibration device 100 according to an embodiment of the present invention is integrally built in or detachably provided in the gas component analyzing apparatus, and more particularly, connected to a supply tube for providing a gas for calibration (hereinafter, referred to as a 'calibration gas') to the separation unit 30.

The supply tube may be a tube corresponding to any one position among tubes including the third tube line L3, the fourth tube line L4, and the fifth tube line L5, which provide the calibration gas to the separation unit 30, or a tube directly or indirectly connected to the separation unit 30 to provide the calibration gas.

As illustrated in FIG. 3, the calibration device 100 is configured to sequentially provide a plurality of calibration gases having concentrations different from each other to the separation unit 30 through the supply tube. As the calibration device 100 may sequentially provide the plurality of calibration gases, calibration data for calibrating the gas sensor 40 may be acquired.

In detail, the calibration device 100 includes: one side connection part V100 and L100 that is selectively connected to one point of the supply tube; the other side connection part V200 and L300 that is selectively connected to the other point of the supply tube; and a calibration line part 110 to 150, 110V1 to 150V1, and 110V2 to 150V2 including a plurality of connection tubes 110 to 150 parallel-connecting the one side connection part V100 and L100 to the other side connection part V200 and L300 in different paths from each other. Here, the plurality of connection tubes 110 to 150 have volumes different from each other. Meanwhile, a control unit 60 is provided to control a flow of the calibration gas or the air through the one side connection part V100 and L100, the other side connection part V200 and L300, and the calibration line part 110 to 150, 110V1 to 150V1, and 110V2 to 150V2.

Firstly, the one side connection part V100 and L100 will be described.

The one side connection part V100 and L100 may include one side valve V100 disposed on the supply tube and an input tube L100 that is selectively communicated with the supply tube through the one side valve V100.

For example, as illustrated in FIG. 3, the one side valve V100 may include a three-way solenoid valve connecting each of a rear end of the third tube line L3, a front end of the sampling loop 20, and the input tube L100.

The one side valve V100 selectively performs an open-close operation so that the calibration gas and the air provided through the third tube line L3 are provided to the sampling loop 20 or the input tube L100.

Thereafter, the other side connection part V200 and L300 will be described.

The other side connection part V200 and L300 may include the other side valve V200 disposed on the supply tube and the output tube L300 that is selectively communicated with the supply tube through the other side valve V200.

For example, as illustrated in FIG. 3, the other side valve V200 may include a three-way solenoid valve connecting each of a rear end of the sampling loop 20, the fourth tube line L4, and the output tube L300.

The other side valve V200 selectively performs an open-close operation so that the calibration gas and the air provided through the rear end of the sampling loop 20 or the output tube L300 are provided to the fourth tube line L4.

Thereafter, the calibration line part 110 to 150, 110V1 to 150V1, and 110V2 to 150V2 will be described.

The calibration line part 110 to 150, 110V1 to 150V1, and 110V2 to 150V2 includes: a plurality of input side calibration valves 110V1 to 150V1 that are serially arranged on the input tube L100; a plurality of output side calibration valves 110V2 to 150V2 that are serially arranged on the output tube L300; and a plurality of connection tubes 110 to 150 one-to-one connecting the plurality of input side calibration valves 110V1 to 150V1 to the plurality of output side calibration valves 110V2 to 150V2 in parallel to each other.

For example, as illustrated in FIG. 3, the plurality of input side calibration valves 110V1 to 150V1 may include the three-way solenoid valves that are serially arranged on the input tube L100, and the three-way solenoid valves may have one ports, among three ports, respectively connected to the plurality of output side calibration valves 110V2 to 150V2 through the plurality of connection tubes 110 to 150.

Also, the plurality of output side calibration valves 110V2 to 150V2 may include the three-way solenoid valves that are serially arranged on the output tube L300, and the three-way solenoid valves may have one ports, among three ports, respectively connected to the plurality of input side calibration valves 110V1 to 150V1 through the plurality of connection tubes 110 to 150.

Meanwhile, the plurality of connection tubes 110 to 150 one-to-one connecting the plurality of input side calibration valves 110V1 to 150V1 to the plurality of output side calibration valves 110V2 to 150V2 in parallel to each other may have volumes different from each other. For example, as tubes having the same diameter have the lengths different from each other, the plurality of connection tubes may have volumes different from each other.

When a standard volume is V, each of the plurality of connection tubes may have a ratio below.

First connection tube 110: $\frac{1}{16} \times V$

Second connection tube 120: $\frac{1}{8} \times V$

Third connection tube 130: $\frac{1}{4} \times V$

Fourth connection tube 140: $\frac{1}{2} \times V$

Fifth connection tube 150: $1 \times V$

As described above, the connection tubes 110 to 150 each have the volume different from each other, so as to generate the calibration gas having a plurality of concentrations by using the calibration gas having a single concentration. In detail, the concentration of each of the calibration gases injected according to each of volume fractions are generated as intended concentration.

For example, when the sampling loop 20 has a volume of V, and measurement is performed by using an amount corresponding to the volume of V, the calibration gas having a concentration of 1,000 ppb is used, and the fifth connection tube 150 has the same volume of V as that of the sampling loop 20, the fifth connection tube 150 generates the calibration gas having the concentration of 1,000 ppb, the fourth connection tube 140 generates the calibration gas having the concentration of 500 ppb that is one-half of 1,000 ppb, the third connection tube 130 generates the calibration gas having the concentration of 250 ppb that is one-fourth of 1,000 ppb, the second connection tube 120 generates the calibration gas having the concentration of 125 ppb that is one-eighth of 1,000 ppb, and the first connection tube 110 generates the calibration gas having the concentration of 62.5 ppb that is one-sixteenth of 1,000 ppb. Accordingly, a calibration equation corresponding a range within 1000 ppb may be calculated as in FIG. 16A.

While, in the related art, the calibration gas having various concentrations is prepared generally on the basis of a ratio of dilution of the concentration of each of the calibration gases instead of a constant volume of the used calibration gas, in the present invention, although the dilution ratios of the calibration gases are the same as each other, as the volume of the used calibration gas is adjusted, as a result, the calibration gases each having different concentrations may be achieved to obtain the same result as that when the diluted calibration gas is used in the related art.

Meanwhile, when the sampling loop 20 has a volume of V, and measurement is performed by using an amount corresponding to the volume of V, the calibration gas having a concentration of 1,000 ppb is used, and the fifth connection tube 150 has the volume of 2×V that is two times of the volume of the sampling loop 20, the fifth connection tube 150 generates the calibration gas having the concentration of 2,000 ppb, the fourth connection tube 140 generates the calibration gas having the concentration of 1,000 ppb that is one-half of 2,000 ppb, the third connection tube 130 generates the calibration gas having the concentration of 500 ppb that is one-fourth of 2,000 ppb, the second connection tube 120 generates the calibration gas having the concentration of 250 ppb that is one-eighth of 2,000 ppb, and the first connection tube 110 generates the calibration gas having the concentration of 125 ppb that is one-sixteenth of 2,000 ppb. Accordingly, a calibration equation corresponding a range within 2,000 ppb may be calculated as in FIG. 16B, and this calibration equation have two-times wider range than that of the calibration equation described above.

In consideration of the above description, the calibration equation corresponding to the wide range may be calculated by using the calibration gas having a low concentration. For example, when the sampling loop 20 has the volume of V, and the measurement is performed by using an amount corresponding to the volume of V, the calibration gas having the concentration of 500 ppb, and when the fifth connection tube 150 has the volume of 2×V, the measurement is performed by using an amount corresponding to the volume of V, the calibration gas having the concentration of 500 ppb, and the fifth connection tube 150 has the volume of 2×V that is two-times of the volume of the sampling loop 20, the calibration equation for the same range as that of FIG. 16A may be calculated by using the calibration gas having the low concentration.

The volume ratio between the sampling loop 20 and the fifth connection tube 150 may be 1:0.1 to 1:10, desirably, 1:1 to 1:3 in consideration of the diameter of the connection tube and the concentration of the calibration gas.

Meanwhile, the connection tubes 110 to 150 may be desirably configured to sequentially discharge the calibration gases such that the calibration gas that is firstly introduced is firstly discharged. To this end, the connection tubes 110 to 150 may have a diameter small enough in comparison with a total length of the connection tubes. For example, each of the connection tubes 110 to 150 may have a diameter equal to or less than 10 mm and have a length that is ten-times or more of the diameter thereof.

As described above, when the connection tubes 110 to 150 are configured to sequentially discharge the calibration gas in the method in which the calibration gas that is firstly introduced is firstly discharged, the volume of the plurality of connection tubes 110 to 150 may be formed by various shapes such that the tubes having the same length are formed to have diameters different from each other, or an expansion portion having a volume different from that of the tube may be formed in the middle of tubes having the same length and same diameter.

Meanwhile, the volume of the plurality of connection tubes 110 to 150 may be formed by various shapes such that the tubes having the same length are formed to have diameters different from each other, or an expansion portion having a volume different from that of the tube may be formed in the middle of tubes having the same length and same diameter.

Meanwhile, an exhaust tube L200 connecting an end of the input tube L100 forming the one side connection part V100 and L100 and an end of the output tube L300 forming the other side connection part V200 and L300 may be further provided. In detail, the exhaust tube L200 may detour to be connected to the fifth input side calibration valve 150V1 and the fifth output side calibration valve 150V2.

Meanwhile, according to another embodiment, as illustrated in FIG. 15, the calibration line part may include: an input side multi-directional selection valve 100V1 having one input port P1 communicating with the input tube L100 and a plurality of output ports P2 selectively connected to the input port P1; an output side multi-directional selection valve 100V2 having one output port P3 communicating with the output tube L300 and a plurality of input port P4 selectively connected to the output port P3; and a plurality of connection tubes 110' to 150' one-to-one connecting the plurality of output ports P2 of the input side multi-directional selection valve 100V1 to the plurality of input port P4 of the output side multi-directional selection valve 100V2 in parallel to each other.

The input side multi-directional selection valve 100V1 may selectively open one output port P2 among the plurality of output ports P2, and the output side multi-directional selection valve 100V2 may selectively open one input port P4 among the plurality of input ports P4.

Detailed operation of the calibration line part will be described together with the control operation of the control unit 60 that will be described later.

Thereafter, the control unit 60 will be described.

The control unit 60 serves to control a flow of the gas or the air through the above-described one side connection part V100 and L100, the other side connection part V200 and L300, and the calibration line part 110 to 150, 110V1 to 150V1, and 110V2 to 150V2 and, in detail, controls a flow direction of each of the one side valve V100, the other side valve V200, the input side calibration valves 110V1 to 150V1, and the output side calibration valves 110V2 to 150V2.

Firstly, the control unit 60 controls to fill the calibration gas for sequential calibration to the plurality of connection tubes 110 to 150 through the control of the input side calibration valves 110V1 to 150V1 and the output side calibration valves 110V2 to 150V2 in a state in which the gas is able to be introduced into the calibration line part 110 to 150, 110V1 to 150V1, and 110V2 to 150V2 through the control of the one side valve V100 and the other side valve V200.

In detail, the flow direction of each of the one side valve V100 and the other side valve V200 is controlled so that the third tube line L3 communicates with the input tube L100, and the output tube L300 is connected to the fourth tube line L4 to allow the gas to be introduced into the calibration line part 110 to 150, 110V1 to 150V1, and 110V2 to 150V2.

In the above-described state, as illustrated in FIG. 4, as the calibration gas flows through the first connection tube 110 by controlling the input side calibration valve 110V1 and the output side calibration valve 110V2 to communicate with each other through the first connection tube 110, the calibration gas is filled in the first connection tube 110.

Thereafter, as illustrated in FIG. 5, as the second input side calibration valve 120V1 is connected through the first input side calibration valve 110V1, the second output side calibration valve 120V2 is connected through the first output side calibration valve 110V2, and the second input side calibration valve 120V1 and the second output side calibration valve 120V2 communicate with each other through the second connection tube 120, the calibration gas flows through the second connection tube 120 to fill the calibration gas into the second connection tube 120.

Thereafter, as illustrated in FIG. 6, as the third input side calibration valve 130V1 is connected through the first and second input side calibration valves 110V1 and 120V1, the third output side calibration valve 130V2 is connected through the first and second output side calibration valves 110V2 and 120V2, and the third input side calibration valve 130V1 and the third output side calibration valve 130V2 communicate with each other through the third connection tube 130, the calibration gas flows through the third connection tube 130 to fill the calibration gas into the third connection tube 130.

Thereafter, as illustrated in FIG. 7, as the fourth input side calibration valve 140V1 is connected through the first, second, and third input side calibration valves 110V1, 120V1, and 130V1, the fourth output side calibration valve 140V2 is connected through the first, second, and third output side calibration valves 110V2, 120V2, and 130V2, and the fourth input side calibration valve 140V1 and the fourth output side calibration valve 140V2 communicate with each other through the fourth connection tube 140, the calibration gas flows through the fourth connection tube 140 to fill the calibration gas into the fourth connection tube 140.

Thereafter, as illustrated in FIG. 8, as the fifth input side calibration valve 150V1 is connected through the first, second, third, and fourth input side calibration valves 110V1, 120V1, 130 V1, and 140V1, the fifth output side calibration valve 150V2 is connected through the first, second, third, and fourth output side calibration valves 110V2, 120V2, 130 V2, and 140V2, and the fifth input side calibration valve 150V1 and the fifth output side calibration valve 150V2 communicate with each other through the fifth connection tube 150, the calibration gas flows through the fifth connection tube 150 to fill the calibration gas into the fifth connection tube 150.

When the above-described process is completed, the first connection tube 110, the second connection tube 120, the third connection tube 130, the fourth connection tube 140, and the fifth connection tube 150 are filled with the calibration gas.

In the above-described state, as illustrated in FIG. 9, the air is controlled to circulate to the exhaust tube L200 through the first, second, third, fourth, and fifth input side calibration valves 110V1, 120V1, 130 V1, 140V1, and 150V1 and the first, second, third, fourth, and fifth output side calibration valves 110V2, 120V2, 130 V2, 140V2, and 150V2, the calibration gas except for the calibration gas in the first connection tube 110, the second connection tube 120, the third connection tube 130, the fourth connection tube 140, and the fifth connection tube 150 may be discharged.

When the above-described process is completed, the calibration gas is filled only in the first connection tube 110, the second connection tube 120, the third connection tube 130, the fourth connection tube 140, and the fifth connection tube 150.

In the above-described state, as illustrated in FIG. 10, as the first input side calibration valve 110V1 and the first output side calibration valve 110V2 are controlled to communicate with each other through the first connection tube 110, the air may be provided to the first connection tube 110, and, accordingly, the measurement using the calibration gas in the first connection tube 110 may be possible. A valve measured by using the calibration gas in the first connection tube 110 is transmitted to the control unit 60 and saved as Y1.

Thereafter, as illustrated in FIG. 11, as the calibration device is controlled such that the second input side calibration valve 120V1 is connected through the first input side calibration valve 110V1, the second output side calibration valve 120V2 is connected through the first output side calibration valve 110V2, and the second input side calibration valve 120V1 and the second output side calibration valve 120V2 communicate with each other through the second connection tube 120, the air may be provided to the second connection tube 120, and, accordingly, the measurement using the calibration gas in the second connection tube 120 may be possible. A valve measured by using the calibration gas in the second connection tube 120 is transmitted to the control unit 60 and saved as Y2.

Thereafter, as illustrated in FIG. 12, as the calibration device is controlled such that the third input side calibration valve 130V1 is connected through the first and second input side calibration valve 110V1 and 120V1, the third output side calibration valve 130V2 is connected through the first and second output side calibration valve 110V2 and 120V2, and the third input side calibration valve 130V1 and the third output side calibration valve 130V2 communicate with each other through the third connection tube 130, the air may be provided to the third connection tube 130, and, accordingly, the measurement using the calibration gas in the third connection tube 130 may be possible. A valve measured by using the calibration gas in the third connection tube 130 is transmitted to the control unit 60 and saved as Y3.

Thereafter, as illustrated in FIG. 13, as the calibration device is controlled such that the fourth input side calibration valve 140V1 is connected through the first, second, and third input side calibration valve 110V1, 120V1, and 130V1, the fourth output side calibration valve 140V2 is connected through the first, second, and third output side calibration valve 110V2, 120V2, and 130V2, and the fourth input side calibration valve 140V1 and the fourth output side calibration valve 140V2 communicate with each other through the fourth connection tube 140, the air may be provided to the fourth connection tube 140, and, accordingly, the measurement using the calibration gas in the fourth connection tube 140 may be possible. A valve measured by using the calibration gas in the fourth connection tube 140 is transmitted to the control unit 60 and saved as Y4.

Thereafter, as illustrated in FIG. 14, as the calibration device is controlled such that the fifth input side calibration valve 150V1 is connected through the first, second, third, and fourth input side calibration valves 110V1, 120V1, 130 V1, and 140V1, the fifth output side calibration valve 150V2 is connected through the first, second, third, and fourth output side calibration valves 110V2, 120V2, 130 V2, and 140V2, and the fifth input side calibration valve 150V1 and the fifth output side calibration valve 150V2 communicate with each other through the fifth connection tube 150, the air may be provided to the fifth connection tube 150, and, accordingly, the measurement using the calibration gas in the fifth connection tube 150 may be possible. A valve measured by using the calibration gas in the fifth connection tube 150 is transmitted to the control unit 60 and saved as Y5.

When the above-described process is completed, the calibration gases having different concentrations from each other, which are filled in the first connection tube 110, the second connection tube 120, the third connection tube 130, the fourth connection tube 140, and the fifth connection tube 150, are sequentially transferred to the detector to perform the detection to acquire the five calibration data including Y1, Y2, Y3, Y4, and Y5 corresponding to five-times detection as illustrated in FIG. 16.

Meanwhile, when the input side multi-directional selection valve (100V1 in FIG. 15) and the output side multi-directional selection valve (100V2 in FIG. 15) are provided, the five calibration data corresponding to the five-times detection may be acquired in such a manner that the calibration gas is sequentially filled in a first connection tube 110', a second connection tube 120', a third connection tube 130', a fourth connection tube 140', and a fifth connection tube 150', and then the calibration gases in the first connection tube 110', the second connection tube 120', the third connection tube 130', the fourth connection tube 140', and the fifth connection tube 150' are sequentially transferred.

Meanwhile, although a case of using the five connection tubes 110 to 150 and 110' to 150' is exemplarily described, the number of connection tubes may increase according to the desired number of the calibration data.

As described above, the process of calibrating the gas component analyzing apparatus by using the five calibration data acquired through the five-times detection may include, e.g., storing the five calibration data in a memory provided in the gas component analyzing apparatus, calculating the data stored in the memory by the control unit provided in the gas component analyzing apparatus to produce a calibration equation, reflecting the produced calibration equation to generate a new firmware by the control unit provided in the gas component analyzing apparatus, and updating the newly generated firmware to update.

As described above, the process of calibrating the gas component analyzing apparatus by using the five calibration data acquired through the five-times detections may be performed by the control unit 60.

While the present invention has been particularly shown and described with reference to the accompanying drawings according to exemplary embodiments, it will be understood by those of ordinary skill in the art that various changes in form and details may be made therein without departing from the spirit and scope of the present invention as defined by the following claims.

The invention claimed is:

1. A calibration device comprising:
a first connection part connected to a first supply tube which provides a calibration gas, the first connection part including an input valve connected to the first supply tube and an input tube configured to be selectively communicated with the first supply tube through the input valve;
a second connecting part connected to a second supply tube which provides the calibration gas, the second connection part including an output valve connected to the second supply tube and an output tube configured to be selectively communicated with the second supply tube through the output valve; and
a calibration line part connecting the first connection part to the second connection part and configured to adjust a volume ratio of the calibration gas, the calibration line part including a plurality of input side calibration valves that are serially arranged on the input tube, a plurality of output side calibration valves that are serially arranged on the output tube, and a plurality of connection tubes one-to-one connecting the plurality of input side calibration valves to the plurality of output side calibration valves in parallel, wherein the plurality of connection tubes have different volumes from each other; and a controller configured to control the input valve to introduce the calibration gas into the input tube from the first supply tube, control the plurality of input side calibration valves to sequentially fill the calibration gas flowing through the input tube in the plurality of connection tubes, control the plurality of output side calibration valves to sequentially discharge the calibration gas filled in the plurality of connection tubes, and control the output valve to discharge the calibration gas flowing through the output tube into the second supply tube.

2. The calibration device of claim 1, further comprising an exhaust tube connecting an end of the first connection part to an end of the second connection part, wherein air circulates through the input tube, the exhaust tube, and the output tube to discharge and remove the calibration gas except for the calibration gas filled in the connection tubes.

3. The calibration device of claim 2, wherein the calibration gas filled in the plurality of connection tubes is sequentially transferred to a detector so as to acquire calibration data.

4. The calibration device of claim 1, wherein a connection tube having a largest volume among the plurality of connection tubes has the same volume as that of a sampling loop provided in a gas component analyzing apparatus.

5. The calibration device of claim 1, wherein a connection tube having a largest volume among the plurality of connection tubes has a volume greater than that of a sampling loop provided in a gas component analyzing apparatus.

6. A gas component analyzing apparatus comprising the calibration device, which is described in claim 1, integrally embedded or detachably provided therein.

7. A calibration device comprising:

a first connection part connected to a first supply tube which provides a calibration gas, the first connection part including an input valve connected to the first supply tube and an input tube configured to be selectively communicated with the first supply tube through the input valve;

a second connecting part connected to a second supply tube which provides the calibration gas, the second connection part including an output valve connected to the second supply tube and an output tube configured to be selectively communicated with the second supply tube through the output valve; and a calibration line part connecting the first connection part to the second connection part and configured to adjust a volume ratio of the calibration gas, the calibration line part including an input side multi-directional selection valve having a first input port communicating with the input tube and a plurality of second output ports that are selectively connected to the first input port, an output side multi-directional selection valve having a third output port communicating with the output tube and a plurality of fourth input ports that are selectively connected to the third output port, and a plurality of connection tubes one-to-one connecting the plurality of second output ports of the input side multi-directional selection valve to the plurality of fourth input ports of the output side multi-directional selection valve each other, wherein the plurality of connection tubes have different volumes from each other; and a controller configured to control the input valve to introduce the calibration gas into the input tube from the first supply tube, control the plurality of second output ports of the input side multi-directional selection valve to sequentially fill the calibration gas flowing through the input tube in the plurality of connection tubes, control the plurality of fourth input ports of the output side multi-directional selection valve to sequentially discharge the calibration gas filled in the plurality of connection tubes, and control the output valve to discharge the calibration gas flowing through the output tube into the second supply tube.

* * * * *